United States Patent
Chung et al.

(10) Patent No.: US 12,024,540 B2
(45) Date of Patent: Jul. 2, 2024

(54) POLYPETIDE, PHOTORESIST COMPOSITION INCLUDING THE SAME, AND METHOD OF FORMING PATTERN USING THE SAME

(71) Applicant: Samsung Electronics Co., Ltd., Suwon-si (KR)

(72) Inventors: Soonchun Chung, Seoul (KR); Ginam Kim, Seongnam-si (KR); Jieun Kim, Suwon-si (KR); Jinha Kim, Hwaseong-si (KR); Joonsong Park, Suwon-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 142 days.

(21) Appl. No.: 17/578,720

(22) Filed: Jan. 19, 2022

(65) Prior Publication Data
US 2022/0372078 A1 Nov. 24, 2022

(30) Foreign Application Priority Data

May 20, 2021 (KR) .................. 10-2021-0064955
Jul. 8, 2021 (KR) .................. 10-2021-0089947

(51) Int. Cl.
C07K 14/00 (2006.01)
G03F 7/039 (2006.01)

(52) U.S. Cl.
CPC ............ *C07K 14/001* (2013.01); *G03F 7/039* (2013.01)

(58) Field of Classification Search
None
See application file for complete search history.

(56) References Cited

U.S. PATENT DOCUMENTS

| | | |
|---|---|---|
| 9,771,400 B2 | 9/2017 | Kurland et al. |
| 2005/0090641 A1 | 4/2005 | Valluzzi et al. |
| 2008/0145862 A1 | 6/2008 | Cabezas |
| 2010/0120116 A1 | 5/2010 | Kaplan et al. |
| 2016/0222174 A1 | 8/2016 | Widmaier et al. |
| 2023/0176480 A1* | 6/2023 | Kim .................. G03F 7/039 430/270.1 |
| 2023/0183294 A1* | 6/2023 | Kim .................. G03F 7/0392 514/21.3 |

FOREIGN PATENT DOCUMENTS

| | | | | |
|---|---|---|---|---|
| CN | 102540771 A | 7/2012 | | |
| CN | 107723287 A | 2/2018 | | |
| EP | 294979 A1 | 12/1988 | | |
| EP | 700929 A2 | 3/1996 | | |
| JP | 2005513162 A | 5/2005 | | |
| JP | 2005263631 A | * | 9/2005 | |
| KR | 101688171 B1 | 12/2016 | | |
| WO | 0149834 A2 | 7/2001 | | |
| WO | 2004106359 A2 | 12/2004 | | |
| WO | 2008018749 A1 | 2/2008 | | |
| WO | WO-2015060159 A1 | * | 4/2015 | .......... A01K 67/033 |
| WO | WO-2017138002 A1 | * | 8/2017 | ....... C07K 14/43518 |

OTHER PUBLICATIONS

English Abstract of CN 102540771.
English Abstract of CN 107723287.
English Abstract of KR 20160017295-English translation for KR 101688171.
Extended European Search Report issued Jun. 28, 2022 in EP Patent Application No. 22153597.4, 10 pp.
Freccero, M. et al., Modeling H-Bonding and Solvent Effects in the Alkylation ofPyrimidine Bases by a Prototype Quinone Methide, JACS. 2003, 125, 3544-3553.
Joonhan Park et al., "Eco-friendly photolithography using water developable pure silk fibroin", RSC Adv., 2016, 6, 39330-39334 (DOI: 10.1039/c6ra04516b).
Kim, S. et al. All-water-based electron-beam lithography using silk as a resist. Nature nanotech, vol. 9, Apr. 2014, 306-310.
Laura Albrecht, et al., "Stabilizing effect of solvent and guest residue amino acids on a model alpha-helix peptide", Computational and Theoreical Chemistry, 998, 2012, pp. 80-86.
Miju Kim, et al., "PDMS bonding to a bio-friendly photoresist via self-polymerized poly adhesive for complex protein micropatterring inside microfluidic channels", Colloids and Surface B:Biointerfaces, vol. 112, 2013, pp. 134-138.
Seassal, C. et al. InP bonded membrane photonics components and circuits: toward 2.5 dimensional micro-nano-photonics, ResearchGate, IEEE J. Sel. Top. Quantum Electron, Apr. 2005, vol. 11, No. 2, 395-407.
Shibu Chameettachal, et al., Regulation of Chondrogenesis and Hypertrophy in SilkFibroin-Gelatin-Based 3D Bioprinted Constructs, ACS Biomater. Sci. Eng. 2016, 2, 1450-1463.
Tetsuo Asakura, et al., "Possible Implications of Serine and Tyrosine Residues and Intermolecular Interactions on the Appearance of Silk I Structure of Bombyx Mori Silk Fibroin-Derived Synthetic Peptides: High-Resolution 13 C Cross-Polarization/Magic-Angle Spinning NMR Study" vol. 6, No. 1, 2005, 468-474, XP55932018; 2004_991065_824951759_1.

* cited by examiner

*Primary Examiner* — Sudhakar Katakam
*Assistant Examiner* — Zachary J Miknis
(74) *Attorney, Agent, or Firm* — CANTOR COLBURN LLP

(57) ABSTRACT

A polypeptide, a photoresist composition including the polypeptide, a photoresist including the polypeptide, and a method of forming patterns using the photoresist composition.

19 Claims, 5 Drawing Sheets

Specification includes a Sequence Listing.

# POLYPETIDE, PHOTORESIST COMPOSITION INCLUDING THE SAME, AND METHOD OF FORMING PATTERN USING THE SAME

CROSS-REFERENCE TO RELATED APPLICATIONS

This application claims priority to Korean Patent Application Nos. 10-2021-0064955, filed on May 20, 2021, and 10-2021-0089947, filed on Jul. 8, 2021, in the Korean Intellectual Property Office under 35 U.S.C. § 119, and all the benefits accruing therefrom, the disclosures of which are incorporated by reference herein in their entirety.

BACKGROUND

1. Field

Embodiments of the present disclosure relate to a polypeptide, a photoresist composition including the polypeptide, and a method of forming patterns using the photoresist composition.

2. Description of the Related Art

The demand for high-integration of semiconductor devices has contributed to a growing need for finer and more precise patterning in the manufacture of such devices. Materials that can be chemically amplified are routinely used for photoresists; however, acid diffusion in such materials can often be an obstacle to achieving the fine patterns. Moreover, the materials used to develop the photoresists may also be toxic or hazardous to human health as well as hazardous to the environment.

Accordingly, there is a demand for eco-friendly photoresist materials which are suitable for achieving fine patterns and release little, if any, chemicals that may adversely affect human health or the environment.

SUMMARY

Provided are polypeptides, the polypeptides as a photoresist, and a photoresist composition including the polypeptides. In addition, provided is a method of forming eco-friendly patterns using the photoresist composition.

Additional aspects will be set forth in part in the description which follows and, in part, will be apparent from the description, or may be learned by practice of the presented embodiments of the disclosure.

According to an aspect of an embodiment, a polypeptide includes a region A and a region B, wherein the region A has an alanine content of 20 percent (%) or more and includes at least one first repeat unit having a sequence of 4 to 10 consecutive amino acid residues, and the region B has a tyrosine content of 10% or more and includes at least one second repeat unit having a sequence of 4 to 10 consecutive amino acid residues.

A ratio of the number of repetitions of the first repeat unit to the number of repetitions of the second repeat unit may be about 1:1 to about 1:x, where x is a real number greater than 1.

A ratio of the number of repetitions of the first repeat unit to the number of repetitions of the second repeat unit may be about 1:1 to about 1:4.

The first repeat unit may be represented by Formula 1, and the second repeat unit may be represented by Formula 2:

$$X_{11}\text{-}(Ala\text{-}X_{12})_{n11}\text{-}X_{13} \qquad \text{Formula 1}$$

$$X_{21}\text{-}(X_{22}\text{-}X_{23})_{n21}\text{-}Tyr \qquad \text{Formula 2}$$

In Formulas 1 and 2,
$X_{11}$ and $X_{12}$ are each independently Gly or Ala,
$X_{13}$ is Ser or Ala, and n11 is an integer of 1 to 4,
$X_{21}$ and $X_{23}$ are each independently Gly or Ala,
$X_{22}$ is Gly, Ala, or Val, and n21 is an integer of 1 to 4.
$X_{11}$ and $X_{12}$ may be Gly, $X_{13}$ may be Ser, and n11 may be 1 or 2.
$X_{21}$ and $X_{23}$ may be Gly, $X_{22}$ may be Gly or Val, and n21 may be 1, 2, or 3.

The first repeat unit may be Gly-Ala-Gly-Ala-Gly-Ser (SEQ ID NO:1), and the second repeat unit may be Gly-Ala-Gly-Ala-Gly-Tyr (SEQ ID NO:2), Gly-Ala-Gly-Val-Gly-Ala-Gly-Tyr (SEQ ID NO:3), Gly-Ala-Gly-Tyr (SEQ ID NO:4), or Gly-Ala-Gly-Ala-Gly-Ala-Gly-Tyr (SEQ ID NO:5).

The polypeptide may further include a region H including Gly-Ala-Ala-Ser (SEQ ID NO:6).

The region H may be represented by Formula 3:

$$X_{31}\text{-}(Ala\text{-}X_{32})_{n31}\text{-}X_{33}\text{-}Gly\text{-}Ala\text{-}Ala\text{-}Ser \qquad \text{Formula 3}$$

In Formula 3,
$X_{31}$ and $X_{32}$ are each independently Gly or Ala,
$X_{33}$ is Ser or Ala, and n31 is 1 or 2 (SEQ ID NO:7).
The region H may be Gly-Ala-Gly-Ala-Gly-Ser-Gly-Ala-Ala-Ser (SEQ ID NO:8).

The polypeptide may have a polydispersity index of 2 or less.

The polypeptide may have a weight average molecular weight of 10,000 grams per mole or less.

According to an aspect of another embodiment, a photoresist including the polypeptide described above.

According to an aspect of another embodiment, a photoresist composition includes the polypeptide described above and water.

The photoresist composition may have a polypeptide concentration of about 0.1 percent weight per volume (w/v %) to about 20 w/v %.

According to an aspect of another embodiment, a method of forming patterns includes applying and heating the photoresist composition described above to form a photoresist film; exposing at least a portion of the photoresist film to high-energy radiation; and developing the exposed photoresist film, e.g., by using a developer.

The heating may be performed at about 50° C. to about 95° C.

The high-energy radiation may have a wavelength of 200 nm or less.

The source of the high-energy radiation may be an excimer laser having a wavelength of 200 nm or less, e.g., ArF excimer laser having a wavelength of 193 nm.

The developer may comprise or consist of water.

The exposed portion of the photoresist film may be water-soluble, and the non-exposed portion of the photoresist film may be water-insoluble.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
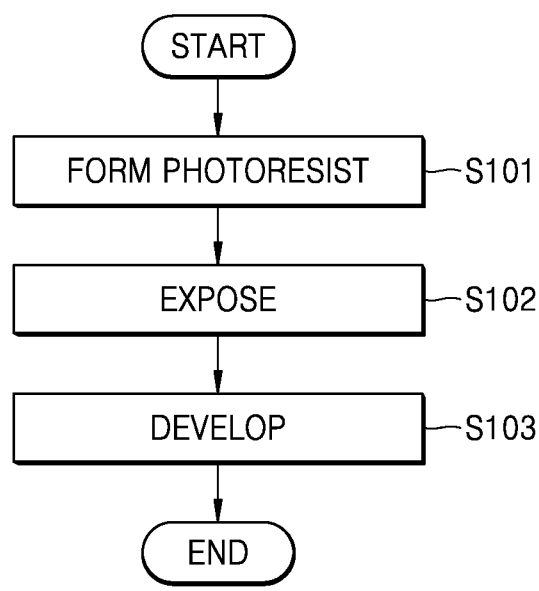
FIG. 1 is a flowchart showing a method of forming patterns in a substrate, according to an embodiment of the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, e.g., by referring to the figures, to explain aspects of the embodiments. As used herein, the term "and/or" includes any and all combinations of one or more of the associated listed items. Expressions such as "at least one of," when preceding a list of elements, modify the entire list of elements and do not modify the individual elements of the list.

The present disclosure may be modified in various forms and have many embodiments, and particular embodiments are illustrated in the drawings and are described in the detailed description. However, this does not intent to limit the present disclosure within particular embodiments, and it should be understood that the present disclosure covers all the modifications, equivalents, and replacements within the idea and technical scope of the present disclosure. In describing the present disclosure, detailed descriptions of related known art will at time be omitted.

It will be understood that when an element is referred to as being "on" another element, it can be directly on the other element or intervening elements may be present therebetween. In contrast, when an element is referred to as being "directly on" another element, there are no intervening elements present.

It will be understood that, although the terms "first", "second", "third", etc., may be used herein to describe various elements, components, regions, layers, and/or sections, these elements, components, regions, layers and/or sections should not be limited by these terms. These terms are only used to distinguish one element, component, region, layer, and/or section, from another element, component, region, layer, and/or section should not be limited by these terms. Thus, "a first element", "component", "region", "layer", or "section" discussed below could be termed a second element, component, region, layer or section without departing from the teachings herein.

As used herein, the singular forms "a," "an," and "the" are intended to include the plural forms, including "at least one," unless the context clearly indicates otherwise. "At least one" is not to be construed as limiting "a" or "an." "Or" means "and/or." As used herein, the term "and/or" includes any and all combinations of one or more of the associated listed items.

It will be further understood that, unless specifically stated otherwise, the terms "comprise" or "comprising" when used herein, specify the presence of stated features, numbers, steps, operations, elements, parts, components, materials, or combinations thereof, but do not preclude the presence or addition of one or more other features, numbers, steps, operations, elements, parts, components, materials, or combinations thereof.

Wherever a range of values is recited, that range includes every value falling within the range, as if written out explicitly, and further includes the values bounding the range. Thus, a range of "from X to Y" includes every value falling between X and Y, and includes X and Y. "About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±5%, or within ±1% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein Hereinafter, embodiments of the present disclosure are described in detail with reference to the accompanying drawings, and when describing the present disclosure with reference to the drawings, substantially identical or corresponding components are given with the same reference numerals, and their duplicated descriptions will be omitted. In the drawings, the thicknesses of layers and regions are enlarged for clear explanation. In addition, in the drawings, the thicknesses of some layers and regions are exaggerated for convenience of description. Meanwhile, embodiments described herein are merely examples and can be embodied in various forms based on these examples.

Polypeptide

As used herein, the term "repeat unit" refers to a sequence of four or more consecutive amino acid residues in a continuous stretch within a polypeptide, and also refers to a subsequence that is repeated within a larger sequence. In this case, it is not necessary that only sequences with identical repeat units be repeated. Repeat units may include variable compositional elements, and due to the variable compositional elements, each repeat unit may vary randomly within the same region.

As used herein, the term "region" refers to a sequence of four or more consecutive amino acid residues in a continuous stretch within a polypeptide and includes at least one repeat unit.

A polypeptide according to example embodiments includes a region A and a region B, wherein the region A has an alanine content of 20% or more and includes at least one first repeat unit having a sequence of 4 to 10 consecutive amino acid residues, and the region B has a tyrosine content of 10% or more and includes at least one second repeat unit having a sequence of 4 to 10 consecutive amino acid residues.

In an embodiment, the region A and the region B may be sequentially arranged in the polypeptide. That is, the polypeptide may have no other sequence present between the region A and the region B, and an N-terminal of the region A and a C-terminal of the region B may form a peptide bond. Accordingly, the polypeptide may consist of the region A and the region B. In another embodiment, the polypeptide may consist essentially of the region A and the region B.

The polypeptide includes a sequence of 4 or more, 6 or more, 10 or less, or 8 or less amino acid residues within each repeat unit.

The polypeptide may include 1 to 20 repeat units within each region. Specifically, the region A may include 1 to 7 first repeat units, and the region B may include 1 to 20 second repeat units. More specifically, the region A may include 1 or more, 2 or more, 3 or more, 7 or less, 6 or less, or 4 or less first repeat units, and the region B may include 1 or more, 2 or more, 4 or more, 6 or more, 20 or less, 16 or less, 12 or less, or 8 or less second repeat units.

In an embodiment, a ratio of the number of repetitions of the first repeat unit to the number of repetitions of the second repeat unit may be about 1:1 to about 1:x, where x may be a real number greater than 1. Specifically, x may be a real number of 10 or less. More specifically, x may be a real number of 10 or less, 9 or less, 8 or less, 7 or less, or 6 or less. More specifically, a ratio of the number of repetitions of the first repeat unit to the number of repetitions of the second repeat unit may be about 1:1 to about 1:4. In particular, a ratio of the number of repetitions of the first repeat unit to the number of repetitions of the second repeat unit may be about 1:4. When the ratio of the number of repetitions of the first repeat unit to the number of repetitions of the second repeat unit satisfies the range described above, a photoresist composition having both improved photosensitivity and pattern quality may be provided.

In an embodiment, the polypeptide may have a weight average molecular weight of 10,000 grams per mole (g/mol) or less, and specifically, the polypeptide may have a molecular weight of about 3000 g/mol to about 10,000 g/mol. The polypeptide is clearly different from proteins that form fibers having a molecular weight of greater than 10,000 g/mol. When the polypeptide has a molecular weight of greater than 10,000 g/mol, the polypeptide may have reduced solubility in solvents, particularly water, and thus may not be suitable for preparing a photoresist composition and may not have a satisfactory viscosity for applying the photoresist composition to a substrate. When the molecular weight of the polypeptide satisfies the range described above, the polypeptide may have a viscosity and/or solubility suitable for use as a photoresist composition. As used herein, "molecular weight" refers to a weight average molecular weight.

In an embodiment, the polypeptide may have a polydispersity index of 2 or less. Specifically, the polypeptide may have a polydispersity index of 1. The polypeptide is not obtained by being extracted from natural proteins, and instead, is obtained by using a microorganism-based protein production technology, and thus may have a low polydispersity index. The fact that the polydispersity index of the polypeptide is relatively low may provide suitable conditions for use as a photoresist composition, such as improved resolution, reduced LER, and/or reduced LWR.

In an embodiment, the polypeptide may have a crystallinity of 40% or more. Specifically, the polypeptide may have a crystallinity of 43% or more. When the crystallinity satisfies the range described above, a reduced LER, and/or reduced LWR may be provided.

The region A may include alanine (Ala). Specifically, the region A may have an alanine content of 20 percent (%) or more and may include at least one first repeat unit having a sequence of 4 to 10 consecutive amino acid residues, and thus the region A may have an alanine content of 20% or more, 25% or more, 30% or more, 35% or more, 40% or more, 50% or less, or 45% or less. The first repeat unit may have an alanine content of 20% or more, 25% or more, 30% or more, 35% or more, 40% or more, 50% or less, or 45% or less. In this case, the alanine content in the region A is calculated based on a percentage of the number of alanine among the number of total amino acid residues in a region, e.g., the region A. Likewise, the alanine content in the first repeat unit is calculated based on the percentage of the number of alanine among the number of all amino acid residues constituting the first repeat unit. The region A may include a sequence that may form a β-strand. Without wishing to be bound by theory, the region A includes alanine, and thus may be relatively hydrophobic, and may form a crystalline region believed to be formed by β-sheet stacking.

The region B may include tyrosine (Tyr). Specifically, the region B may have a tyrosine content of 10% or more and may include at least one first repeat unit having a sequence of 4 to 10 consecutive amino acid residues, and thus the region B may have a tyrosine content of 10% or more, 15% or more, 20% or more, 25% or more, 30% or more, 40% or less, or 35% or less. The second repeat unit may have a tyrosine content of 10% or more, 15% or more, 20% or more, 25% or more, 30% or more, 40% or less, or 35% or less. Likewise, the tyrosine content in the region B is calculated based on the percentage of the number of tyrosine among the number of total amino acid residues in the region B. Likewise, the tyrosine content in the second repeat unit is calculated based on the percentage of the number of tyrosine among the number of all amino acid residues constituting the second repeat unit. The region B may include a sequence responsive to high-energy radiation. Without wishing to be bound by theory, the region B includes tyrosine, and thus may respond to light of 200 nm or less, specifically light of 193 nm. In particular, in the region B, when exposed to high-energy radiation, a bond between a phenyl ring of tyrosine and a main backbone chain is broken to form quinone methide, and the quinone methide breaks a hydrogen bond between the β-sheets of the region A, thereby causing changes in solubility of the polypeptide in water. That is, the presence of the region B changes the solubility of the polypeptide in water following exposure to high-energy radiation.

In an embodiment, the first repeat unit may be represented by Formula 1 below:

$$X_{11}\text{-}(Ala\text{-}X_{12})_{n11}\text{—}X_{13} \qquad \text{Formula 1}$$

In Formula 1,
$X_{11}$ and $X_{12}$ are each independently Glycine (Gly) or Ala,
$X_{13}$ is Serine (Ser) or Ala, and n11 is an integer of 1 to 4.
Specifically, in Formula 1, $X_{11}$ and $X_{12}$ may be Gly, $X_{13}$ may be Ser, and n11 may be 1 or 2.

More specifically, the first repeat unit may be Gly-Ala-Gly-Ala-Gly-Ser (SEQ ID NO:1).

In an embodiment, the second repeat unit may be represented by Formula 2:

$$X_{21}\text{—}(X_{22}\text{—}X_{23})_{n21}\text{-}Tyr \qquad \text{Formula 2}$$

In Formula 2,
$X_{21}$ and $X_{23}$ are each independently Gly or Ala,
$X_{22}$ is Gly, Ala, or Valine (Val), and n21 is an integer of 1 to 4.

Specifically, in Formula 2, $X_{21}$ and $X_{23}$ may be Gly, $X_{22}$ may be Gly or Val, and n21 may be 1, 2, or 3.

More specifically, the second repeat unit may be Gly-Ala-Gly-Ala-Gly-Tyr (SEQ ID NO:2), Gly-Ala-Gly-Val-Gly-Ala-Gly-Tyr (SEQ ID NO:3), Gly-Ala-Gly-Tyr (SEQ ID NO:4), or Gly-Ala-Gly-Ala-Gly-Ala-Gly-Tyr (SEQ ID NO:5).

In an embodiment, the polypeptide may further include a region H including Gly-Ala-Ala-Ser (SEQ ID NO:6). Specifically, the region A may be interposed between the region H and the region B. In the polypeptide, the region H, the region A, and the region B are consecutively arranged. That is, the polypeptide may have no other sequence present between the region H and the region A, and between the region A and the region B, and an N-terminal of the region H and a C-terminal of the region A may be a peptide bond. In another embodiment, the polypeptide may comprise or consist of the region H, the region A, and the region B.

The region H may include a sequence of 4 to 10 consecutive amino acid residues. The region H may be represented by Formula 3:

$$X_{31}\text{-}(Ala\text{-}X_{32})_{n31}\text{---}X_{33}\text{-}Gly\text{-}Ala\text{-}Ala\text{-}Ser \qquad \text{Formula 3}$$

In Formula 3, $X_{31}$ and $X_{32}$ are each independently Gly or Ala, $X_{33}$ is Ser or Ala, and n31 is 1 or 2 (SEQ ID NO:7).

Specifically, the region H may be Gly-Ala-Gly-Ala-Gly-Ser-Gly-Ala-Ala-Ser (SEQ ID NO:8).

Photoresist Composition

A photoresist composition according to example embodiments may include the polypeptide described above and water. In addition, relatively small amounts of non-toxic organic compounds, e.g., low molecular weight alcohols, may also be present in a photoresist composition.

In an embodiment, the photoresist composition may consist of the polypeptide described herein and water. Unlike photoresist compositions of the related art including organic solvents, matrix materials, and the like, in the photoresist composition, polypeptide and water may serve as a photoresist composition by themselves. The use of peptide and water, which are eco-friendly materials, as a photoresist composition may reduce the frequency of exposure to toxic substances in semiconductor manufacturing processes, make the disposal of waste liquid generated after the semiconductor manufacturing processes easy, and take low costs. In addition, the photoresist composition is not a chemically amplified photoresist, and accordingly, does not cause image degradation due to acid diffusion, which is a shortcoming of the chemically amplified photoresist, and thus may form precise patterns.

The photoresist composition may have a polypeptide concentration of about 0.1 percent weight to volume (w/v %) to about 20 w/v %. Specifically, the photoresist composition may have a polypeptide concentration of about 0.5 w/v % to about 10 w/v %.

Method of Forming Patterns

Figure 2:
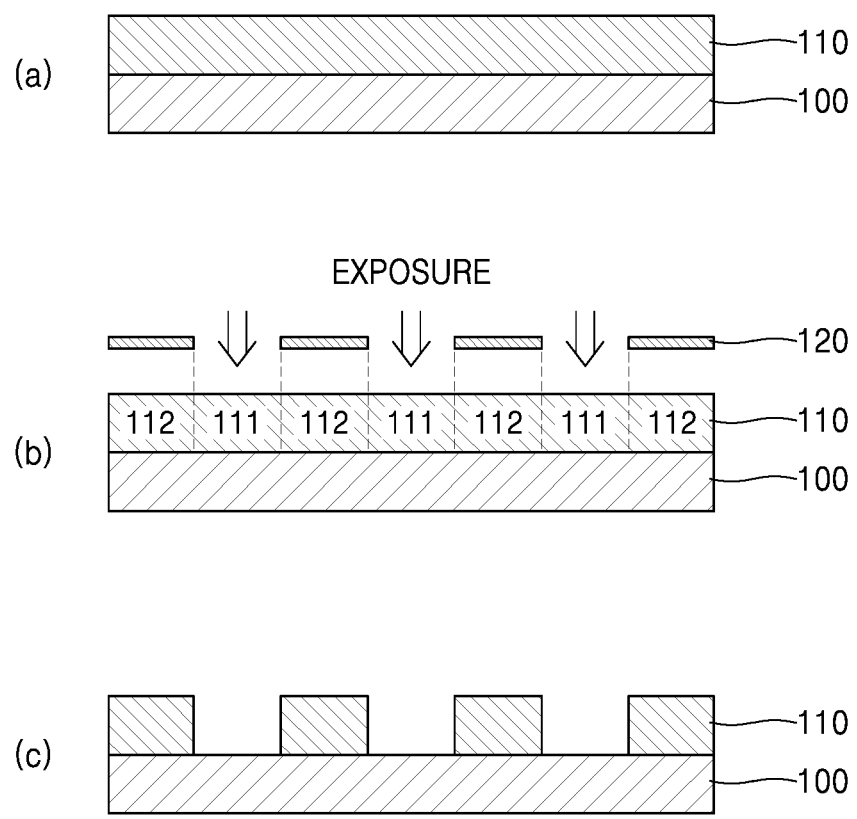
FIG. 2 is a side cross-sectional representation showing a method of forming patterns in a substrate, according to an embodiment of the present disclosure.

Hereinafter, a method of forming patterns according to example embodiments will be described in more detail with reference to FIGS. 1 and 2. FIG. 1 is a flowchart showing a method of forming patterns, according to the example embodiments, and FIG. 2 is a side cross-sectional representation showing a method of forming patterns according to the example embodiments.

Referring to FIG. 1, a method of forming patterns includes applying and heating a photoresist composition as described herein to form a photoresist film (S101); exposing at least a portion of the photoresist film to high-energy radiation (S102); and developing the exposed photoresist film using a developer (S103).

First, a substrate 100 is provided (e.g., commercially available substrate) or is prepared. Examples of the substrate 100 may include semiconductor substrates such as a silicon substrate or a germanium substrate, glass, quartz, ceramic, copper, or the like. In some embodiments, the substrate 100 may include a Group III-V compound such as GaP, GaAs, GaSb, or the like.

A photoresist composition may be specifically applied to the substrate 100 to a desired thickness through a coating method to form a preliminary photoresist film (not shown), and the preliminary photoresist film may be heated to form a photoresist film 110. Examples of the coating method may include spin coating, dipping, roller coating, or other common coating methods. Among the methods, particularly, spin coating may be used, and the photoresist film 110 having a desired thickness may be formed by regulating the viscosity, concentration, and/or spin speed of the photoresist composition. Specifically, the photoresist film 110 may have a thickness of about 10 nm to about 300 nm. More specifically, the photoresist film 110 may have a thickness of about 30 nm to about 200 nm.

When the photoresist composition is applied to the substrate 100, the polypeptide may be water-soluble due to the fact that the polypeptide has a molecular structure in the form of a random coil, and has weak intermolecular attractions. When the polypeptide is water-soluble, it is required to go through a process of making the polypeptide water-insoluble to perform positive-tone development using water in a development process which will be described later. In this case, a method of heating a preliminary photoresist film to remove moisture may be used. Specifically, when the preliminary photoresist film is heated to remove moisture, the region A of the polypeptide may form a hydrogen bond and become crystallized into a β-sheet structure, and accordingly, the polypeptide may become water-insoluble.

The heating may be performed at about 50° C. to about 95° C., specifically, at about 80° C. to about 95° C. Heating at a relatively high temperature may increase the extent of crystallinity of the polypeptide, thereby providing reduced LER and/or reduced LWR.

The heating may be performed at a relative humidity of about 92% or greater.

The heating may be performed for about 1 hour to 20 hours, specifically, 2 hours or more, 4 hours or more, 6 hours or more, or 16 hours or more.

Before the applying of the photoresist composition to the substrate 100, an etching target film (not shown) may be further formed on the substrate 100. The etching target film may refer to a layer in which images are transferred from photoresist patterns and converted into predetermined patterns. In an embodiment, the etching target film may be formed to include, for example, insulating materials such as silicon oxide, silicon nitride, or silicon oxynitride. In some embodiments, the etching target film may be formed to include conductive materials such as metal, metal nitride, metal silicide, or a metal silicide nitride film. In some embodiments, the etching target film may be formed to include semiconductor materials such as polysilicon.

In an embodiment, an antireflection film and a photoresist film may be sequentially formed on the etching target film.

Thereafter, at least a portion of the photoresist film 110 may be exposed using high-energy radiation. For example, at least a portion of the photoresist film 110 may be irradiated with high-energy radiation passing through a mask 120. Accordingly, the photoresist film 110 may have an exposed portion 111 and a non-exposed portion 112. As described above, the bond between the phenyl ring of tyrosine and the main backbone chain is broken due to the exposure to the high-energy radiation to provide an exposed portion 111 of the photoresist film 110, and thereby, form quinone methide. It is believed that the quinone methide breaks the hydrogen bond between the β-sheets of the region A to change the solubility of the polypeptide in water, and thus the polypeptide becomes water-soluble. Accordingly, the exposed portion 111 may be water-soluble and the non-exposed portion 112 may be water-insoluble, and thus the non-exposed portion 112 is not removed by the developer, thereby providing a positive-tone development.

The high-energy radiation may have a wavelength of 200 nm or less. Specifically, a source of the high-energy radiation may be an excimer laser, e.g., an AF excimer laser having a wavelength of 193 nm or an ozone lamp having a wavelength of 184.9 nm. More specifically, the high-energy radiation may be ArF excimer laser having a wavelength of 193 nm.

In an embodiment, ArF excimer laser irradiation may be performed for about 2 minutes to 10 minutes. In this case, an amount of irradiation per minute may be about 4 millijoules per square centimeter ($mJ/cm^2$) to about 60 $mJ/cm^2$, specifically, about 10 $mJ/cm^2$ to about 20 $mJ/cm^2$.

Next, the exposed photoresist film 110 may be developed using a developer. The exposed portion 111 is water-soluble, and accordingly, the exposed portion 111 may be washed off by the developer, if for example, the developer comprises water or water alone is used as a developer. The non-exposed portion 112 remains water-insoluble, and accordingly, remains without being washed off by the developer to form a desired pattern in the photoresist.

Examples of the developing method may include methods such as spin coating, dipping, or puddle coating, and the developing may take time to effectively remove the exposed portion 111, specifically may take about 5 seconds to about 2 minutes, more specifically, about 1 minute.

In an embodiment, the developer may comprise or consist of water. When a developer consisting of water is used, the crystallized photoresist film 110 may be less affected by the developer. Accordingly, it may be easier to control the photoresist film 110 to a desired thickness than when using a developer including other organic solvents other than water, for example, methanol. In addition, since water is used as the developer and no additional additives are required, water may serve both developing and cleaning together to provide simplified processes, reduced cost and time, in addition to maintaining a similar exposure time and similar productivity to processes of the related art across the processes. In particular, it may possibly reduce exposure to toxic substances in semiconductor factories, which is currently causing trouble.

The method of forming patterns according to an embodiment of the present disclosure may further include baking, etching, stripping, and the like, which are performed in a general photolithography process.

EXAMPLES

Synthesis Example 1: Synthesis of Polypeptide $HA_1B_4$

The following method was used to synthesize a polypeptide having a sequence of $HA_1B_4$ shown in Table 1.

Synthesis Examples 2 to 8: Synthesis of Polypeptide

Polypeptides were synthesized in the same manner as in Synthesis Example 1, except that nucleotide sequences for preparing polypeptides of Synthesis Examples 2 to 8 described in Table 1 were used.

TABLE 1

| Example | Poly-peptide | Sequence |
|---|---|---|
| Synthesis Example 1 | HA1B4 | GAGAGSGAAS-$[GAGAGS]_1$-GAGAGY-GAGVGAGY-GAGY-GAGAGAGY |
| Synthesis Example 2 | HA4B4 | GAGAGSGAAS-$[GAGAGS]_4$-GAGAGY-GAGVGAGY-GAGY-GAGAGAGY |
| Synthesis Example 3 | $HA_8B_4$ | GAGAGSGAAS-$[GAGAGS]_8$-GAGAGY-GAGVGAGY-GAGY-GAGAGAGY |
| Synthesis Example 4 | HA12B4 | GAGAGSGAAS-$[GAGAGS]_{12}$-GAGAGY-GAGVGAGY-GAGY-GAGAGAGY |
| Synthesis Example 5 | HA4B0 | GAGAGSGAAS-$[GAGAGS]_4$ |
| Synthesis Example 6 | HA4B2 | GAGAGSGAAS-$[GAGAGS]_4$-GAGAGY-GAGVGAGY |
| Synthesis Example 7 | HA4B3 | GAGAGSGAAS-$[GAGAGS]_4$-GAGAGY-GAGVGAGY-GAGY |

In Table 1, G is Gly, A is Ala, S is Ser, and Y is Tyr; and [GAGAGS]m indicates that GAGAGS (SEQ ID NO:1) sequence is repeated m times.

NcoI and XhoI restriction enzyme cleavage sites were set to be present at both ends of nucleotide sequence for preparing $HA_1B_4$ polypeptide of Table 1, and were loaded into pUC57 vector to synthesize pUC57-$HA_1B_4$ vector. The synthesized pUC57-$HA_1B_4$ vector was treated with ThermoFisher Fermentas™ NcoI and XhoI restriction enzymes, electrophoresed on Bio-Rad Certified Molecular Biology Agarose gel, and the gel was taken out and eluted with GeneAll Hybrid-Q™ to obtain $HA_1B_4$ synthetic gene DNA. pET30a vector DNA was obtained in the same manner as described above, mixed with the previously obtained $HA_1B_4$ synthetic gene DNA, and treated with Takara T4 DNA ligase at 16° C. for 2 hours. Thereafter, the treated $HA_1B_4$ synthetic gene DNA was mixed with HITTM-DH5a competent cells, and the mixture was subjected to heat shock at 42° C. for 30 seconds to introduce DNA into the cells, and plated on LB solid medium containing kanamycin to obtain a colony into which a vector cloned with the synthetic gene in pET30a was introduced. The obtained colony was inoculated in 3 milliliters (mL) of LB liquid medium containing kanamycin and then shaking-cultured at 37° C. and 250 rpm overnight. The inoculated colony was then subjected to miniprep with GeneAll Hybrid-Q™ to obtain a vector, and the obtained vector was treated with ThermoFisher Fermentas™ NcoI and XhoI restriction enzymes, electrophoresed on Bio-Rad Certified Molecular Biology Agarose gel containing AB materials SafeView™, and observed through Bio-Rad GelDoc XR+ system to confirm that the synthetic gene was cloned into pET30a. Using such a method, a pET30a-$HA_1B_4$ vector into which the synthetic gene DNA was introduced was prepared and confirmed.

The pET30a-$HA_1B_4$ vector was mixed with Invitrogen BL21(DE3) competent cells, and the mixture was subjected to heat shock at 42 °C for 30 seconds to introduce DNA into the cells. The cells are then plated on LB solid medium containing kanamycin to obtain a colony. The obtained colony was inoculated in 3 mL of LB liquid medium containing kanamycin and then shaking-cultured at 37° C. and 250 rpm overnight. Then 100 microliters (μl) of the resulting culture solution was inoculated in 10 mL of LB liquid medium containing kanamycin, grown to $OD_{600}$=0.5 at 37° C. and 250 rpm, and further cultured at 37° C. and 250 rpm for 2 hours after 30 ul of 100 mM IPTG was added. resulting colony was subjected to centrifugation at 5000 rpm for 10 minutes to collect the colony. The collected colony was resuspended in 700 μl of a pH8.0 Tris-CI solution, and the cells were disrupted for 2 minutes at an amplitude of 25% using Sonics VCX-130 Ultrasonicator, and subjected to centrifugation at 15,000 rpm for 10 minutes to obtain a supernatant. 75 μl of the supernatant and 25 μl of Bio-Rad 4× Laemmli Sample Buffer™ were mixed and treated at 95° C. for 5 minutes, and 15 μl of the mixture was loaded on Bio-Rad Any-KD™ gel, electrophoresed at 200 V for 30 minutes using a Bio-Rad Mini-PROTEAN device, and stained with Bio-Rad Coomassie Brilliant Blue R-250 Staining Solution to confirm the expression of the synthetic gene. Using such method, a protein-producing colony was prepared, and the expression was confirmed.

The colony confirmed to have the desired polypeptide expression was inoculated in 50 mL of LB liquid medium containing kanamycin and then shaking-cultured at 37° C. and 250 rpm overnight. Then 100 μl of the resulting culture solution was inoculated in 1 L of LB liquid medium containing kanamycin, grown to $OD_{600}$=0.5 at 37° C. and 250 rpm, and then further cultured at 37° C. and 250 rpm for 3 hours after 300 ul of 1 M IPTG was added. The obtained colony was subjected to centrifugation at 5000 rpm for 10 minutes to collect the colony, and the collected colony was resuspended in 10 mL of a pH8.0 Tris-CI solution. The cells were disrupted for 5 minutes at an amplitude of 40% using Sonics VCX-750 Ultrasonicator, and subjected to centrifugation at 15,000 rpm for 30 minutes to obtain a supernatant. The obtained supernatant was passed through 1 mL of Qiagen Ni-NTA agarose resin, passed through 15 mL of a pH8.0 Tris-CI solution containing 10 mM imidazole to wash the resin, and lastly the resin was eluted with 3 mL of a pH8.0 Tris-CI solution containing 100 mM imidazole to purify a desired polypeptide. The purified protein solution was concentrated to 2 w/v % to 5 w/v % using Merck Amicon® Stirred Cells™ and Ultracell 1Kda membrane filter. Thermo-Fisher SnakeSkin™ dialysis tubing (3.5K MWCO 16 mm ID) was cut to 7 cm in length, soaked in 500 mL of tertiary distilled water for 15 minutes, and taken out, and the tubing was wash inside and outside three times, 5 mL of a sample was put in the washed tubing, which was closed at both sides with forceps, the dialysis tubing containing the sample concentrated to 2 w/v % to 5 w/v % was put in 1 L of tertiary distilled water and subjected to dialysis at 20° C. for 4 hours by replacing the distilled water with 1 liter (L) of fresh tertiary distilled water every 1 hour to obtain a 4 w/v % polypeptide aqueous solution. The obtained polypeptide aqueous solution was stored at 4° C. prior to use for preparing a thin film. In addition, through MALDI-TOF analysis, the polypeptide aqueous solution was found to have a polydispersity index of 1.0.

Evaluation Example 1: Characteristic Evaluation According to Length of Region A

Photoresist compositions shown in Table 2 were prepared using 4 w/v % of a polypeptide aqueous solution obtained in Synthesis Examples.

TABLE 2

| Name of photoresist | Polypeptide | Concentration (w/v %) |
|---|---|---|
| Examples 1-1 | $HA_1B_4$ | 4 |
| Examples 1-2 | $HA_4B_4$ | 4 |

TABLE 2-continued

| Name of photoresist | Polypeptide | Concentration (w/v %) |
|---|---|---|
| Reference Example 1-1 | $HA_8B_4$ | 4 |
| Reference Example 1-2 | $HA_{12}B_4$ | 4 |

20 μl of the photoresist composition of Table 2 was applied onto a silicon wafer through spin coating, heated for 16 hours in a thermo-hygrostat at 95° C. and 92% humidity, and moisture was removed therefrom on a hot plate at 95° C. for 1 minute to form a photoresist film having a thickness of 50 nanometers (nm) to 200 nm. Crystallinity of the obtained photoresist film was measured using the following method.

Then, a pattern mask was placed on the photoresist film and the pattern mask-applied photoresist film was exposed with changes to an exposure amount of 4.24 millijoules per square centimeter ($mJ/cm^2$) to 60 $mJ/cm^2$ using ArF excimer lasers, subjected to dipping in water for 1 minute, and developed. For the obtained patterns, line width roughness (LWR) and critical dimension (CD) were evaluated as follows.

The pattern mask is manufactured through a lift-off method following lithography using E-beam on a fused silica substrate and has a line-and-space (L/S) pattern of 500 nm. Crystallinity, LWR, and CD values evaluated for Examples 1-1 and 1-2 and Reference Examples 1-1 and 1-2 are shown in Table 3.

Crystallinity Evaluation

A 1.5 cm square silicon wafer was washed for 30 minutes using a Jelight UVO144AX-220 UV-ozone cleaner, coated with 100 ul of 4 w/v % polypeptide aqueous solution obtained in any one Synthesis Example, and spin-coated at 300 RPM for 5 seconds, at 3000 RPM for 40 seconds, and at 500 RPM for 5 seconds using MIDAS Spin Controller. The coated wafer was dried at 95° C. for 1 minute using a Daehan Scientific HP-LP hot plate, and then treated for 16 hours at 95° C. and 92% humidity using an ESPAC SH-661 thermo-hygrostat to perform film formation. The finished film was scanned at intervals of 1.92 cm 1 in the range of 650 cm 1 to 4000 $cm^{-1}$ using Bruker Varian 670 FT-IR ATR to measure FT-IR, and the measured results were converted to 2nd derivation and FSD for amide I moiety (1595 $cm^{-1}$ to 1705 $cm^{-1}$) using Bruker OPUS ver.7.0 program, subjected to curve fitting to analyze a secondary structure of a thin film polypeptide. The secondary structure of the thin film polypeptide was analyzed according to peak positions fitted by FSD as follows: 1610 $cm^{-1}$ to 1625 $cm^{-1}$ and 1696 $cm^{-1}$ to 1704 $cm^{-1}$: β-sheet structure; 1640 $cm^{-1}$ to 1650 $cm^{-1}$: random coil structure; 1650 $cm^{-1}$ to 1660 $cm^{-1}$: α-helix structure; 1660 $cm^{-1}$ to 1695 $cm^{-1}$: β-turn structure. After this analysis, the ratio of the β-sheet structure portion to the amide I moiety was defined as an extent of crystallinity.

LWR Evaluation

Dimensions of 10 sites were measured in the longitudinal direction of pattern lines obtained using atomic-force microscopy equipment, and based on the results, three batches (3σ) of standard deviation (σ) were obtained as line width roughness (LWR). The smaller this value, the less the roughness and patterns having a uniform line width may be obtained.

CD Evaluation

Dimensions of 10 sites were measured in the longitudinal direction of pattern lines obtained using atomic-force microscopy equipment as critical dimension (CD). In the present disclosure, materials were confirmed to have better sensitivity with an increase in this value.

TABLE 3

| Name of photoresist | Polypeptide | Crystallinity (%) | LWR (nm) | CD (nm) |
|---|---|---|---|---|
| Example 1-1 | $HA_1B_4$ | 44.8 | 8 | 520 |
| Example 1-2 | $HA_4B_4$ | 43.2 | 10 | 320 |
| Reference Example 1-1 | $HA_8B_4$ | 34.9 | 11 | 370 |
| Reference Example 1-2 | $HA_{12}B_4$ | 23.8 | 33 | 510 |

Referring to Table 3, the data indicates that when the number of repetitions of the first repeat unit increased from one or four to eight or twelve, the crystallinity of the polypeptide decreased significantly, and the LWR of the polypeptide increased. Moreover, the data results of Table 3 indicate that when the number of repetitions of the second repeat unit remains the same, a polypeptide having relatively high crystallinity may provide a photoresist having improved LWR performance. In particular, Example 1-1 exhibits both improved LWR and CD characteristics.

Evaluation Example 2: Characteristic Evaluation According to Length of Region B

The polypeptide listed was dissolved in water at (4) w/v % to prepare photoresist compositions shown in Table 4.

TABLE 4

| Name of photoresist | Polypeptide | Concentration (w/v %) |
|---|---|---|
| Reference Example 2-1 | $HA_4B_0$ | 4 |
| Reference Example 2-2 | $HA_4B_2$ | 4 |
| Reference Example 2-3 | $HA_4B_3$ | 4 |
| Example 2-1 | $HA_4B_4$ | 4 |
| Example 2-2 | $HA_1B_4$ | 4 |

The photoresist compositions of Table 4 were used in the same manner as in Example 1-1 to form photoresist films, and form patterns. Using the same method as in Example 1-1, for Examples 2-1 and 2-2 and Reference Examples 2-1 to 2-3, crystallinity, LWR and CD values were measured, and results are shown in Table 5.

TABLE 5

| Name of photoresist | Polypeptide | Crystallinity (%) | LWR (nm) | CD (nm) |
|---|---|---|---|---|
| Reference Example 2-1 | $HA_4B_0$ | 43.1 | 16 | 150 |
| Reference Example 2-2 | $HA_4B_2$ | 44.7 | 10 | 220 |
| Reference Example 2-3 | $HA_4B_3$ | 45.4 | 9 | 240 |
| Example 2-1 | $HA_4B_4$ | 43.2 | 10 | 320 |
| Example 2-2 | $HA_1B_4$ | 44.8 | 8 | 520 |

Referring to Table 5, the data indicates that when the number of repetitions of the second repeat unit increased, the CD of the polypeptide increased. Moreover, the data results of Table 5 show that when the number of repetitions of the first repeat unit remains the same, a photoresist having improved CD performance may be provided with an increase in the number of repetitions of the second repeat unit. In particular, Example 2-2 showed both improved LWR and CD characteristics.

Evaluation Example 3: Comparison with Commercial Photoresist

Figure 3A:
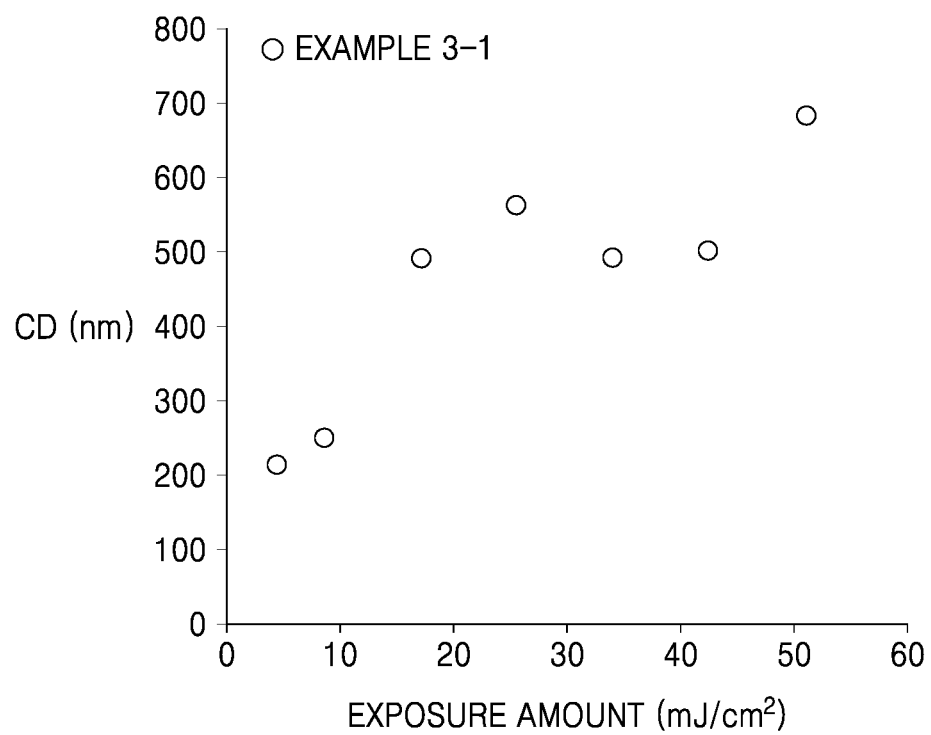
FIGS. 3A to 3C are plots of CD, DT, and LWR data according to radiation exposure of a photoresist that includes Example 3-1.
Figure 3B:
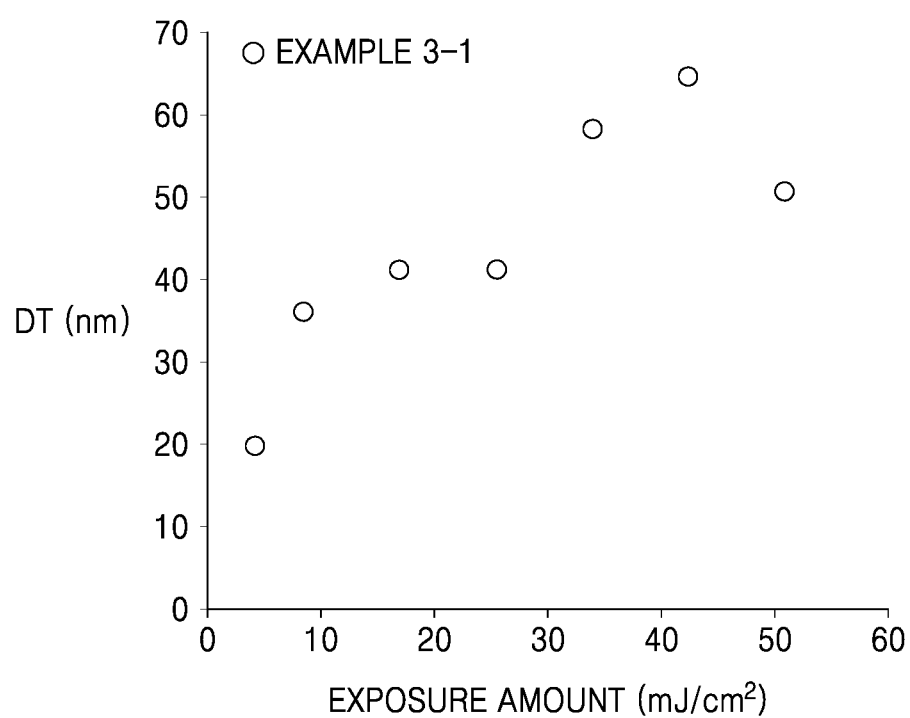
Figure 3C:
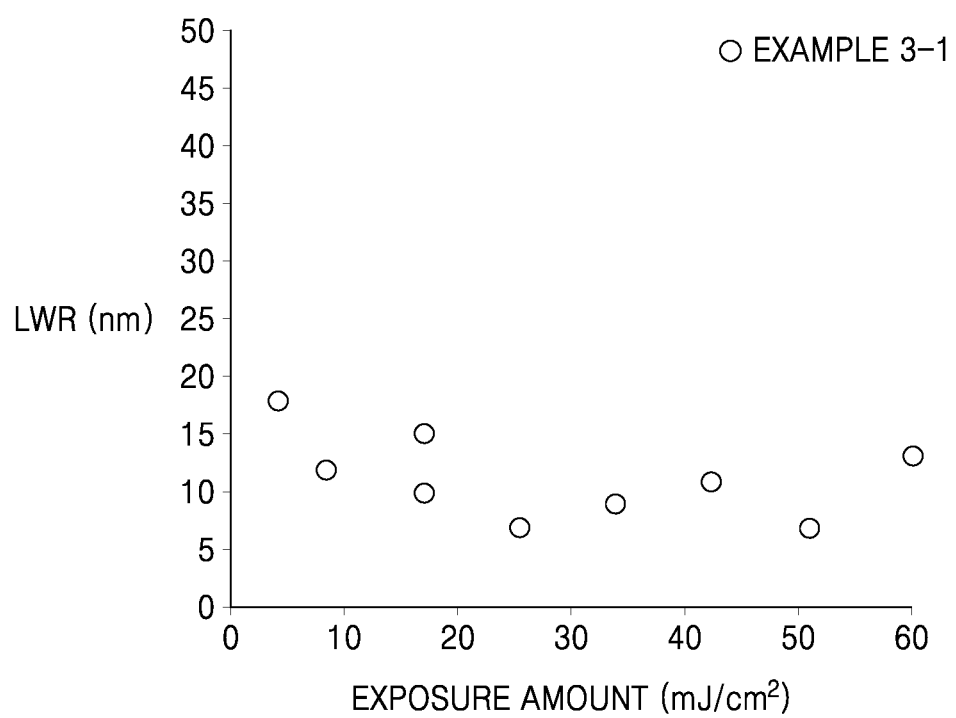

For each of a photoresist composition (Example 3-1) obtained by dissolving the polypeptide obtained from Synthesis Example 1 in water at 4 w/v % and a photoresist composition (Reference Example 3-1) obtained in the same manner as disclosed in RSC Adv., 6, 39330-39334 (2016), a photoresist film having a thickness of 150 nm was formed. A pattern mask having 500 nm line and space (L/S) patterns was placed on the obtained photoresist film and the pattern mask-applied photoresist film was exposed with changes to an exposure amount of 4.24 mJ/cm$^2$ to 60 mJ/cm$^2$ using ArF excimer lasers and developed. LWR, developed thickness (DT), and CD were evaluated for the obtained patterns, and some of the results are shown in FIGS. 3A to 3C.

In particular, Example 3-1 exhibits a performance of CD: 520 nm, DT: 41.1 nm, and LWR: 8 nm at an exposure amount of 20 mJ/cm$^2$, whereas Reference Example 3-1 exhibits a performance of CD: 250 nm, DT: 35 nm, and LWR: 9 nm at an exposure amount of 20 mJ/cm$^2$.

An embodiment of the present disclosure may provide a photoresist composition having improved sensitivity, improved LWR and/or CD. In addition, when patterns are formed using the photoresist composition, manufacturing processes are simplified and disposal cost for generated by-products are also reduced, and thus, manufacturing costs may be reduced.

The present disclosure has been described with reference to embodiments shown in the drawings, this is only for illustrative purposes, and therefore, those skilled in the art will appreciate that various modifications and other equivalent embodiments may be made therein without departing from the spirit and scope as defined by the following claims. Accordingly, the technical scope of the inventive concept should be defined by the technical spirit of the claims. Moreover, it should be understood that embodiments described herein should be considered in a descriptive sense only and not for purposes of limitation. Descriptions of features or aspects within each embodiment should typically be considered as available for other similar features or aspects in other embodiments.

What is claimed is:

1. A polypeptide comprising a region A and a region B, wherein the region A has an alanine content of 20 percent or more and includes at least one first repeat unit having a sequence of 4 to 10 consecutive amino acid residues, and the region B has a tyrosine content of 10 percent or more and includes at least one second repeat unit having a sequence of 4 to 10 consecutive amino acid residues, wherein the first repeat unit is represented by Formula 1, and the second repeat unit is represented by Formula 2:

$$X_{11}\text{-}(Ala\text{-}X_{12})_{n11}\text{---}X_{13}; \qquad \text{Formula 1}$$

$$X_{21}\text{---}(X_{22}\text{---}X_{23})_{n21}\text{-}Tyr; \qquad \text{Formula 2}$$

wherein in Formula 1 and 2,
$X_{11}$ and $X_{12}$ are each independently Gly or Ala,
$X_{13}$ is Ser or Ala, and n11 is an integer of 1 to 4,
$X_{21}$ and $X_{23}$ are each independently Gly or Ala,
$X_{22}$ is Gly, Ale, or Val, and n21 is an integer of 1 to 4, and
the polypeptide has a weight average molecular weight of 10,000 grams per mole or less.

2. The polypeptide of claim 1, wherein a ratio of the number of repetitions of the first repeat unit to the number of repetitions of the second repeat unit is about 1:1 to about 1:x, where x is a real number greater than 1.

3. The polypeptide of claim 1, wherein a ratio of the number of repetitions of the first repeat unit to the number of repetitions of the second repeat unit is about 1:1 to about 1:4.

4. The polypeptide of claim 1, wherein
the first repeat unit is represented by
Gly-Ala-Gly-Ala-Gly-Ser (SEQ ID. NO: 1) or Gly-Ala-Gly-Ala-Gly-Ala-Gly-Ser (SEQ ID. NO:16).

5. The polypeptide of claim 1, wherein the second repeat unit is represented by
Gly-$(X_{22}$-Gly$)_{n21}$-Tyr,
wherein
$X_{22}$ is Gly or Val, and n21 is 1, 2, or 3.

6. The polypeptide of claim 1, wherein the first repeat unit is Gly-Ala-Gly-Ala-Gly-Ser (SEQ ID) NO: 1), and the second repeat unit is Gly-Ala-Gly-Ala-Gly-Tyr (SEQ ID) NO:2), Gly-Ala-Gly-Val-Gly-Ala-Gly-Tyr (SEQ ID NO:3), Gly-Ala-Gly-Tyr (SEQ ID NO:4), or Gly-Ala-Gly-Ala-Gly-Ala-Gly-Tyr (SEQ ID NO:5).

7. The polypeptide of claim 1, further comprising a region H including Gly-Ala-Ala-Ser (SEQ ID NO:6).

8. The polypeptide of claim 7, wherein the region His represented by Formula 3:

$$X_{31}\text{-}(Ala\text{-}X_{32})_{n31}\text{---}X_{33}\text{-}Gly\text{-}Ala\text{-}Ala\text{-}Ser; \qquad \text{Formula 3}$$

wherein in Formula 3,
$X_{31}$ and $X_{32}$ are each independently Gly or Ala,
$X_{33}$ is Ser or Ala, and
n31 is 1 or 2 (SEQ ID NO:7).

9. The polypeptide of claim 7, wherein the region His Gly-Ala-Gly-Ala-Gly-Ser-Gly-Ala-Ala-Ser (SEQ ID NO:1).

10. The polypeptide of claim 1, wherein the polypeptide has a polydispersity index of 2 or less.

11. A photoresist composition comprising: the polypeptide of claim 1; and water.

12. The photoresist composition of claim 11, wherein the photoresist composition has a polypeptide concentration of about 0.1 percent weight per volume to about 20 percent weight per volume.

13. A method of forming patterns, the method comprising:
applying and heating the photoresist composition of claim 11 on a substrate to form a photoresist film;
exposing at least a portion of the photoresist film to high-energy radiation; and
developing the exposed photoresist film.

14. The method of claim 13, wherein the heating is performed at about 50° C. to about 95° C.

15. The method of claim 13, wherein the high-energy radiation has a wavelength of 200 nanometers or less.

16. The method of claim 13, wherein high-energy are ArF excimer lasers having a wavelength of 193 nanometers.

17. The method of claim 13, wherein the developing includes a developer comprising water.

18. The method of claim 13, wherein the exposed portion of the photoresist film is water-soluble, and the non-exposed portion of the photoresist film is water-insoluble.

19. The method of claim 15, wherein the exposure of the tyrosine of region B to the high energy radiation results in bond breakage to form quinone methide, and the quinone methide disrupts a hydrogen bond between the β-sheets of the region so that the polypeptide becomes soluble in water.

* * * * *

SEQUENCE LISTING

<160> NUMBER OF SEQ ID NOS: 15

<210> SEQ ID NO 1
<211> LENGTH: 6
<212> TYPE: PRT
<213> ORGANISM: Artificial Sequence

```
<220> FEATURE:
<223> OTHER INFORMATION: Completely Synthesized

<400> SEQUENCE: 1

Gly Ala Gly Ala Gly Ser
1               5

<210> SEQ ID NO 2
<211> LENGTH: 6
<212> TYPE: PRT
<213> ORGANISM: Artificial Sequence
<220> FEATURE:
<223> OTHER INFORMATION: Completely Synthesized

<400> SEQUENCE: 2

Gly Ala Gly Ala Gly Tyr
1               5

<210> SEQ ID NO 3
<211> LENGTH: 8
<212> TYPE: PRT
<213> ORGANISM: Artificial Sequence
<220> FEATURE:
<223> OTHER INFORMATION: Completely Synthesized

<400> SEQUENCE: 3

Gly Ala Gly Val Gly Ala Gly Tyr
1               5

<210> SEQ ID NO 4
<211> LENGTH: 4
<212> TYPE: PRT
<213> ORGANISM: Artificial Sequence
<220> FEATURE:
<223> OTHER INFORMATION: Completely Synthesized

<400> SEQUENCE: 4

Gly Ala Gly Tyr
1

<210> SEQ ID NO 5
<211> LENGTH: 8
<212> TYPE: PRT
<213> ORGANISM: Artificial Sequence
<220> FEATURE:
<223> OTHER INFORMATION: Completely Synthesized

<400> SEQUENCE: 5

Gly Ala Gly Ala Gly Ala Gly Tyr
1               5

<210> SEQ ID NO 6
<211> LENGTH: 4
<212> TYPE: PRT
<213> ORGANISM: Artificial Sequence
<220> FEATURE:
<223> OTHER INFORMATION: Completely Synthesized

<400> SEQUENCE: 6

Gly Ala Ala Ser
1

<210> SEQ ID NO 7
<211> LENGTH: 10
<212> TYPE: PRT
<213> ORGANISM: Artificial Sequence
<220> FEATURE:
```

```
<223> OTHER INFORMATION: Completely Synthesized
<220> FEATURE:
<221> NAME/KEY: SITE
<222> LOCATION: (1)..(1)
<223> OTHER INFORMATION: X is Gly or Ala
<220> FEATURE:
<221> NAME/KEY: SITE
<222> LOCATION: (3)..(3)
<223> OTHER INFORMATION: X is Gly or Ala
<220> FEATURE:
<221> NAME/KEY: SITE
<222> LOCATION: (5)..(5)
<223> OTHER INFORMATION: X is Gly or Ala
<220> FEATURE:
<221> NAME/KEY: SITE
<222> LOCATION: (6)..(6)
<223> OTHER INFORMATION: X is Ser or Ala

<400> SEQUENCE: 7

Xaa Ala Xaa Ala Xaa Xaa Gly Ala Ala Ser
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Completely Synthesized

<400> SEQUENCE: 8

Gly Ala Gly Ala Gly Ser Gly Ala Ala Ser
1               5                   10

<210> SEQ ID NO 9
<211> LENGTH: 42
<212> TYPE: PRT
<213> ORGANISM: Artificial Sequence
<220> FEATURE:
<223> OTHER INFORMATION: Completely Synthesized

<400> SEQUENCE: 9

Gly Ala Gly Ala Gly Ser Gly Ala Ala Ser Gly Ala Gly Ala Gly Ser
1               5                   10                  15

Gly Ala Gly Ala Gly Tyr Gly Ala Gly Val Gly Ala Gly Tyr Gly Ala
                20                  25                  30

Gly Tyr Gly Ala Gly Ala Gly Ala Gly Tyr
        35                  40

<210> SEQ ID NO 10
<211> LENGTH: 60
<212> TYPE: PRT
<213> ORGANISM: Artificial Sequence
<220> FEATURE:
<223> OTHER INFORMATION: Completely Synthesized

<400> SEQUENCE: 10

Gly Ala Gly Ala Gly Ser Gly Ala Ala Ser Gly Ala Gly Ala Gly Ser
1               5                   10                  15

Gly Ala Gly Ala Gly Ser Gly Ala Gly Ala Gly Ser Gly Ala Gly Ala
                20                  25                  30

Gly Ser Gly Ala Gly Ala Gly Tyr Gly Ala Gly Val Gly Ala Gly Tyr
        35                  40                  45

Gly Ala Gly Tyr Gly Ala Gly Ala Gly Tyr
    50                  55                  60

<210> SEQ ID NO 11
```

<211> LENGTH: 84
<212> TYPE: PRT
<213> ORGANISM: Artificial Sequence
<220> FEATURE:
<223> OTHER INFORMATION: Completely Synthesized

<400> SEQUENCE: 11

Gly Ala Gly Ala Gly Ser Gly Ala Ala Ser Gly Ala Gly Ala Gly Ser
1               5                   10                  15

Gly Ala Gly Ala Gly Ser Gly Ala Gly Ala Ser Gly Ala Gly Ala
            20                  25                  30

Gly Ser Gly Ala Gly Ala Gly Ser Gly Ala Gly Ala Gly Ser Gly Ala
        35                  40                  45

Gly Ala Gly Ser Gly Ala Gly Ala Ser Gly Ala Gly Ala Gly Tyr
    50                  55                  60

Gly Ala Gly Val Gly Ala Gly Tyr Gly Ala Gly Tyr Gly Ala Gly Ala
65                  70                  75                  80

Gly Ala Gly Tyr

<210> SEQ ID NO 12
<211> LENGTH: 108
<212> TYPE: PRT
<213> ORGANISM: Artificial Sequence
<220> FEATURE:
<223> OTHER INFORMATION: Completely Synthesized

<400> SEQUENCE: 12

Gly Ala Gly Ala Gly Ser Gly Ala Ala Ser Gly Ala Gly Ala Gly Ser
1               5                   10                  15

Gly Ala Gly Ala Gly Ser Gly Ala Gly Ala Gly Ser Gly Ala Gly Ala
            20                  25                  30

Gly Ser Gly Ala Gly Ala Gly Ser Gly Ala Gly Ala Gly Ser Gly Ala
        35                  40                  45

Gly Ala Gly Ser Gly Ala Gly Ala Gly Ser Gly Ala Gly Ala Gly Ser
    50                  55                  60

Gly Ala Gly Ala Gly Ser Gly Ala Gly Ala Gly Ser Gly Ala Gly Ala
65                  70                  75                  80

Gly Ser Gly Ala Gly Ala Gly Tyr Gly Ala Gly Val Gly Ala Gly Tyr
            85                  90                  95

Gly Ala Gly Tyr Gly Ala Gly Ala Gly Ala Gly Tyr
        100                 105

<210> SEQ ID NO 13
<211> LENGTH: 34
<212> TYPE: PRT
<213> ORGANISM: Artificial Sequence
<220> FEATURE:
<223> OTHER INFORMATION: Completely Synthesized

<400> SEQUENCE: 13

Gly Ala Gly Ala Gly Ser Gly Ala Ala Ser Gly Ala Gly Ala Gly Ser
1               5                   10                  15

Gly Ala Gly Ala Gly Ser Gly Ala Gly Ala Gly Ser Gly Ala Gly Ala
            20                  25                  30

Gly Ser

<210> SEQ ID NO 14
<211> LENGTH: 48
<212> TYPE: PRT
<213> ORGANISM: Artificial Sequence

```
<220> FEATURE:
<223> OTHER INFORMATION: Completely Synthesized

<400> SEQUENCE: 14

Gly Ala Gly Ala Gly Ser Gly Ala Ala Ser Gly Ala Gly Ala Gly Ser
1               5                   10                  15

Gly Ala Gly Ala Gly Ser Gly Ala Gly Ala Gly Ser Gly Ala Gly Ala
                20                  25                  30

Gly Ser Gly Ala Gly Ala Gly Tyr Gly Ala Gly Val Gly Ala Gly Tyr
        35                  40                  45

<210> SEQ ID NO 15
<211> LENGTH: 58
<212> TYPE: PRT
<213> ORGANISM: Artificial Sequence
<220> FEATURE:
<223> OTHER INFORMATION: Completely Synthesized

<400> SEQUENCE: 15

Gly Ala Gly Ala Gly Ser Gly Ala Ala Ser Gly Ala Gly Ala Gly Ser
1               5                   10                  15

Gly Ala Gly Ala Gly Ser Gly Ala Gly Ala Gly Ser Gly Ala Gly Ala
                20                  25                  30

Gly Ser Gly Ala Gly Ala Gly Ser Gly Ala Gly Ala Gly Tyr Gly Ala
        35                  40                  45

Gly Val Gly Ala Gly Tyr Gly Ala Gly Tyr
        50                  55
```